US005917026A

United States Patent [19]
Löwenadler et al.

[11] Patent Number: 5,917,026
[45] Date of Patent: Jun. 29, 1999

[54] FUSION PROTEINS OF IMMUNOPOTENTIATING ACTIVITY

[76] Inventors: Björn Löwenadler, Gribbylunds Allé 60, S-183 65 Täby; Nils Lycke, Mimersvägen 25, S-433 61 Säevedalen, both of Sweden

[21] Appl. No.: 08/596,482

[22] Filed: Feb. 5, 1996

[51] Int. Cl.[6] .................................................. C07H 21/04
[52] U.S. Cl. ................ 536/23.4; 435/320.1; 435/252.33; 435/240.2; 435/252.3; 424/278.1; 514/885; 530/300; 530/350; 536/23.1
[58] Field of Search .................................. 536/23.1, 23.4; 435/320.1, 252.33, 252.3, 240.2; 514/885; 530/300, 350; 424/278.1

[56] References Cited

U.S. PATENT DOCUMENTS 5,143,844  9/1992  Abrahmsén et al. .

FOREIGN PATENT DOCUMENTS 9108298  6/1991  WIPO .

OTHER PUBLICATIONS

Roit et al "Immunology" 3rd Edition, Mosby Press, St. Louis pp. 1.1–1.12 and 5.10 (1993).
Osband et al Immunology Today vol. 11, No. 6 (1990) pp. 193–195.
Herbert et al (eds) The Dictionary of Immunology, Academic Press, Harcourt Brace & Company, London (1995) pp. 62–63.
Lycke et al Immunology (1986) 59 pp. 301–308.

*Primary Examiner*—Anthony C. Caputa
*Assistant Examiner*—Heather A. Bakalyar
*Attorney, Agent, or Firm*—Burns, Doane, Swecker & Mathis, L.L.P.

[57] ABSTRACT

A DNA-sequence comprising a first sequence coding for a native or mutant subunit of a bacterial toxin that confers enzymatic ADP-ribosylating activity, and a second sequence coding for a peptide such that the resulting fusion protein is in possession of water solubility and capability of targeting the fusion protein to a specific cell receptor different from receptors binding to the native toxin, thereby mediating intracellular uptake of at least said subunit;

fusion proteins coded for by such DNA-sequence;

compositions for use in improving immune functions; and recombinant expression vectors and transformed bacterial cells containing such DNA-sequence.

24 Claims, 4 Drawing Sheets

PCR-primers used for isolation of CTA1
and the D-region of protein A.

```
         E                H
         C                i
         O                n
         R                c
         1                2
         /                /
#1   cagctgaattccgttgacaatgatgataagttatatcg
```

```
         H                S
         i                n
         n                a
         d                B
         3                1
         /                /
#2   gaccgaagcttacgtacgatgatcttggagcattcc
```

```
         B
         a                A
         m                v
         H                a
         I                I
         /                /
#3   ggatccgggaagacacccgaggctgatgcgcaacaaaa
```

```
         E
         c                A
         o                v
         R                a
         I                I
         /                /
#4   agaattcgcctcgggtttcggtgcttgagat
```

Primers #1 and #2 represent PCR-primers used to isolate CTA 1. Bold letters represent CTA 1-specific sequences. Primers #3 and #4 represent PCR-primers used to isolate the D region of protein A. Bold letters represent D region specific sequences.

(1) GENERAL INFORMATION

(i) APPLICANT: LOWANDER, Bjorn
                    LYCKE, Nils     (ii) TITLE OF INVENTION: FUSION PROTEINS OF IMMUNOPOTENTIATING ACTIVITY     (iii) NUMBER OF SEQUENCES: 4

(iv) CORRESPONDENCE ADDRESS:
          (A) ADDRESSE: BURNS, DOANE, SWECKER & MATHIS
          (B) STREET: P.O. BOX 1404
          (C) CITY: ALEXANDRIA
          (D) STATE: VIRGINIA
          (E) COUNTRY: UNITED STATES
          (F) ZIP: 22313-1404

(v) COMPUTER READABLE FORM:
          (A) MEDIUM TYPE: FLOPPY DISK
          (B) COMPUTER: IBM PC COMPATIBLE
          (C) OPERATING SYSTEM: PC-DOS/MS-DOS
          (D) SOFTWARE: PATENTIN RELEASE #1.0, VERSION #1.30

(vi) CURRENT APPLICATION DATA:
          (A) APPLICATION NUMBER: US 08/596,482
          (B) FILING DATE: 05-FEB-1996
          (C) CLASSIFICATION:

(viii) ATTORNEY/AGENT INFORMATION
          (A) NAME: DUFFETT, JR., BENTON S.
          (B) REGISTRATION NUMBER: 22,030
          (C) REFERENCE/DOCKET NUMBER: 003300-369

(ix) TELECOMMUNICATION INFORMATION
          (A) TELEPHONE: (703) 836-6620
          (B) TELEFAX: (703) 836-2021

(2) INFORMATION FOR SEQ. ID NO:1:

(i) SEQUENCE CHARACTERISTICS
          (A) LENGTH: 38 BASE PAIRS
          (B) TYPE: NUCLEIC ACID
          (C) STRANDEDNESS: SINGLE
          (D) TOPOLOGY: LINEAR     (ii) MOLECULE TYPE: DNA (GENOMIC)

(xi) SEQUENCE DESCRIPTION: SEQ ID NO:1:

CAGCTGAATT    CCGTTGACAA    TGATGATAAG    TTATATCG (2) INFORMATION FOR SEQ ID NO:2:

(i) SEQUENCE CHARACTERISTICS:
          (A) LENGTH: 36 BASE PAIRS
          (B) TYPE: NUCLEIC ACID
          (C) STRANDEDNESS: SINGLE
          (D) TOPOLOGY: LINEAR     (ii) MOLECULE TYPE: DNA (GENOMIC)

FIG. 2A (xi) SEQUENCE DESCRIPTION: SEQ ID NO:2:

GACCGAAGCT    TACGTACGAT    GATCTTGGAG    CATTCC (2) INFORMATION FOR SEQ ID NO:3:

(i) SEQUENCE CHARACTERISTICS:
        (A) LENGTH: 38 BASE PAIRS
        (B) TYPE: NUCLEIC ACID
        (C) STRANDEDNESS: SINGLE
        (D) TOPOLOGY: LINEAR     (ii) MOLECULE TYPE: DNA (GENOMIC)

(xi) SEQUENCE DESCRIPTION: SEQ ID NO:3:

GGATCCGGGA    AGACACCCGA    GGCTGATGCG    CAACAAAA (2) INFORMATION FOR SEQ ID NO:4:

(i) SEQUENCE CHARACTERISTICS:
        (A) LENGTH: 31 BASE PAIRS
        (B) TYPE: NUCLEIC ACID
        (C) STRANDEDNESS: SINGLE
        (D) TOPOLOGY: LINEAR     (ii) MOLECULE TYPE: DNA (GENOMIC)

(xi) SEQUENCE DESCRIPTION: SEQ ID NO:4:

AGAATTCGCC    TCGGGTTTCG    GTGCTTGAGA    T

FUSION PROTEINS OF IMMUNOPOTENTIATING ACTIVITY

The present invention relates to DNA-sequences coding for fusion proteins comprising a native or mutant sub-unit of a bacterial toxin, the fusion proteins per se, compositions for use in improving immune functions, and vectors and bacterial cells harboring such DNA-sequences.

BACKGROUND OF THE INVENTION

Introduction

With the growing understanding of surface receptor structure, signal transduction and function of second messenger systems in eukaryotic cells a new realm of regulatory mechanisms have attracted the interest of many scientists. Altering cell function by intervening with the intracellular controlling systems appears to be a powerful and highly efficient way to subdue unwarranted reactions to environmental factors or microbial infections. In immunology it has become increasingly important to control inflammatory reactions in autoimmunity and allergy, to enhance anti-tumor immunity as well as to increase efficiency in vaccine take. Therefore, exploring the possibilities of immunomodulation through signal-transduction and second messengers may open up new therapies and strategies to treat diseases in which the immune system is part of the pathogenic mechanism or important for host resistance against infectious diseases or development of cancer. Also, therapies preventing organ transplant rejection are highly desired and recent findings in experimental animal models have given evidence that immunomodulation may significantly prolong organ transplant survival time.

There is a group of bacterial toxins that exert strong enzymatic activity on mammalian cells. These toxins, of which E coli heat-labile toxin (LT) and cholera toxin (CT) are well known representatives, act by ADP-ribosylation of GTP-binding proteins in the cell membrane of the target cells. In the ADP-ribosylation reaction, NAD+ is split into free nicotinamide and an ADP-ribose moiety is associated with the guanidinium group of an arginine in the a-subunit of the stimulatory G protein (Gs). The Gsa-protein becomes permanently activated and stimulates adenylate cyclase which results in the formation of large quantities of intracellular cAMP. The increase in cAMP may then act to immunomodulate many diverse immune reactions such as increasing B lymphocyte differentiation, augmenting co-stimulation of antigen-presenting cells, inhibiting or promoting various T cell functions or modulating apoptosis in lymphoid cells. There is no more important and ubiquitos intraellular regulatory molecule than cAMP. The mechanism by which cAMP exerts its function is pleiotropic and increases in intracellular cAMP may affect different cells in different ways. Also, cells of a particular cell lineage may respond with inhibited function to cAMP at one stage of differentiation whereas at a different stage strong enhancing effects may be observed. Many genes have been found to be under transcriptional control of cAMP, and cAMP regulatory gene elements have been described.

CT is composed of five enzymatically inactive, non-toxic B-subunits (CTB) held together in a pentamere structure surrounding a single A-subunit that contains a linker to the pentamere via the A2 fragment (CTA2) and the toxic enzymatically active A1-fragment (CTA1) of the molecule. The toxic CTA1 has strong ADP-ribosyl transferase activity and is thought to act on several G-proteins of which the activity is strongest on Gsa. This results in activation of adenylate cyclase and the subsequent intracellular increase in cAMP. CTB binds to the ganglioside GM1-receptor, present on most mammalian cells including lymphocytes and gut epithelial cells, and CTA is thereafter translocated into the cell-membrane/cytosol of the cell where the CTA1 and CTA2 are dissociated. The profuse diarrheal response in cholera is thought to result from CTA1-induced increased cAMP levels in the intestinal epithelium. An important issue is, therefore, whether the immunomodulating property of CT may be separated from the toxic property.

Exploitation of the mucosal immune system offers several advantages from a vaccine point of view. Mucosal vaccines may achieve both systemic and local mucosal immune protection against infectious microorganisms of which many gain access to the body via mucosal membranes There is a growing interest for oral vaccines and for the possibility of using such vaccines to protect against infectious diseases affecting not only mucosal surfaces but also against diseases like HIV, polio etc [Holmgren, J. and Lycke, N. In 11th Nobel Conference; Chartwell-Bratt Ltd, Bromley: 1986; pp 9–22.; Lycke, N. and Svennerholm, A. -M. The presentation of immunogens at the gut and other mucosal surfaces. In The molecular approach to new and improved vaccines.; Woodrow and Levine, Ed.; Marcel Dekker Inc: NY, 1990.]. However, most soluble protein antigens are poorly immunogenic when given alone perorally and, although live vectors have been found to be efficient delivery systems for oral antigen administration, the general use of such vaccines is still unclear [Holmgren, J. and Lycke, N. In 11th Nobel Conference; Chartwell-Bratt Ltd, Bromley: 1986; pp 9–22; Lycke, N. and Svennerholm, A. -M. The presentation of immunogens at the gut and other mucosal surfaces. In The molecular approach to new and improved vaccines.; Woodrow and Levine, Ed.; Marcel Dekker Inc: NY, 1990.] This has prompted research with the aim of identifying mucosal adjuvants that could find general use in non-replicating oral vaccines. A powerful mucosal adjuvant should be non-toxic and greatly improve immunogenicity and generate immunological memory to soluble antigens which are normally poor immunogens when administered perorally [Lycke, N. and Svennerholm, A. -M. The presentation of immunogens at the gut and other mucosal surfaces. In The molecular approach to new and improved vaccines.; Woodrow and Levine, Ed.; Marcel Dekker Inc: NY, 1990.]. Two principally different approaches have been taken to achieve this goal; the first has focused on constructing powerful delivery systems for oral antigens such as encapsulated microparticles or immune stimulating complexes (iscomes) [Challacombe, S. J., Rahman, D., Jeffery, H., Davis, S. S. and O'Hagan, D. T. Enhanced secretory IgA and systemic IgG antibody responses after oral immunization with biodegradable microparticles containing antigen. Immunology. 76, 164–8, 1992.; Eldridge, J., Gilley, R. M., Staas, J. R., Moldevanue, Z., Meulbroek, T. and Tice, T. R. Biodegradable microspheres: vaccine delivery system for oral immunization. In Current topics in Microbiology and Immunology. 1989; Vol. 146; pp 59.]. The second approach is to construct an adjuvant that will modulate and greatly augment the immune response to the oral antigen by evoking strong IgA immunity and immunological memory in the gut mucosa as well as at other mucosal sites [Lycke, N. and Svennerholm, A. -M. The presentation of immunogens at the gut and other mucosal surfaces. In The molecular approach to new and improved vaccines.; Woodrow and Levine, Ed.; Marcel Dekker Inc: NY, 1990.].

Cholera toxin is an exceptionally potent mucosal immunogen and adjuvant [Elson, C. 0. and Ealding, W. Generalized systemic and mucosal immunity in mice after mucosal stimulation with cholera toxin. J Immunol. 132, 2736–41, 1984.; Liang, X. P., Lamm, M. E. and Nedrud, J. G. Oral administration of cholera toxin-Sendai virus conjugate potentiates gut and respiratory immunity against Sendai virus. J Immunol. 141, 1495–501, 1988.; Lycke, N. and Holmgren, J. Strong adjuvant properties of cholera toxin on gut mucosal immune responses to orally presented antigens. Immunology. 59, 301–8, 1986]. The toxin has become the best studied prototype and most used probe to understand how an efficient mucosal adjuvant might be constructed [Lycke, N. and Svennerholm, A. -M. The presentation of immunogens at the gut and other mucosal surfaces. In The molecular approach to new and improved vaccines.; Woodrow and Levine, Ed.; Marcel Dekker Inc: NY, 1990]. Despite several years of research and many reports on immunomodulating properties of CT it is still unclear which entity of CT that is critical for its adjuvant mechanism. The adjuvant properties of CT have been studied in a mouse model using both in vivo and in vitro experimental systems [Lycke, N. and Svennerholm, A. -M. The presentation of immunogens at the gut and other mucosal surfaces. In The molecular approach to new and improved vaccines.; Woodrow and Levine, Ed.; Marcel Dekker Inc: NY, 1990; Lycke, N. and Holmgren, J. Strong adjuvant properties of cholera toxin on gut mucosal immune responses to orally presented antigens. Immunology. 59, 301–8, 1986; Bromander, A., Holmgren, J. and Lycke, N. Cholera toxin stimulates IL-1 production and enhances antigen presentation by macrophages in vitro. J Immunol. 146, 2908–14, 1991.; Hörnqvist, E., Goldschmidt, T. J., Holmdahl, R. and Lycke, N. Host defense against cholera toxin is strongly CD4+ T cell dependent. Infect Immun. 59, 3630–8, 1991; Lycke, N. and Holmgren, J. Long-term cholera antitoxin memory in the gut can be triggered to antibody formation associated with protection within hours of an oral challenge immunization. Scand J Immunol. 25, 407–12, 1987.; Lycke, N. and Strober, W. Cholera toxin promotes B cell isotype differentiation. J Immunol. 142, 3781–7, 1989.; Lycke, N. and Holmgren, J. Adoptive transfer of gut mucosal antitoxin memory by isolated B cells 1 year after oral immunization with cholera toxin. Infect Immun. 57, 1137–41, 1989; Lycke, N., Bromander, A. K., Ekman, L., Karlsson, U. and Holmgren, J. Cellular basis of immuno-modulation by cholera toxin in vitro with possible association to the adjuvant function in vivo. J Immunol. 142, 20–7, 1989; Lycke, N., Karlsson, U., Sjolander, A. and Magnusson, K. E. The adjuvant action of cholera toxin is associated with an increased intestinal permeability for luminal antigens. Scand J Immunol. 33, 691–8, 1991.; Lycke, N., Severinson, E. and Strober, W. Molecular effects of cholera toxin on isotype differentiation. Immunol Res. 10, 407–12, 1991.; Lycke, N., Tsuji, T. and Holmgren, J. The adjuvant effect of Vibrio cholerae and *Escherichia coli* heat-labile enterotoxins is linked to their ADP-ribosyltransferase activity. Eur J Immunol. 22, 2277–81, 1992.; Lycke, N. Y. Cholera toxin promotes B cell isotype switching by two different mechanisms. cAMP induction augments germ-line Ig H-chain RNA transcripts whereas membrane ganglioside GMl-receptor binding enhances later events in differentiation. J Immunol. 150, 4810–21, 1993]. In the research we have tried to systematically address CT's immunomodulating properties on the different events involved in initiating and regulating mucosal immune responses; antigen-presentation, IgA B cell differentiation, T cell regulation and development of long-term immunological memory [Lycke, N. and Svennerholm, A. -M. The presentation of immunogens at the gut and other mucosal surfaces. In The molecular approach to new and improved vaccines.; Woodrow and Levine, Ed.; Marcel Dekker Inc: NY, 1990.; Lycke, N. and Holmgren, J. Adoptive transfer of gut mucosal antitoxin memory by isolated B cells 1 year after oral immunization with cholera toxin. Infect Immun. 57, 1137–41, 1989; Lycke, N., Severinson, E. and Strober, W. Molecular effects of cholera toxin on isotype differentiation. Immunol Res. 10, 407–12, 1991.; Vajdy, M. and Lycke, N. Stimulation of antigen-specific T- and B-cell memory in local as well as systemic lymphoid tissues following oral immunization with cholera toxin adjuvant. Immunology. 80, 197–203, 1993]. Previous data and the finding of an increased gut permeability for luminal antigens in the presence of CT suggested that the adjuvant effect might depend on the ability of CT, but not CTB, to activate the adenylate cyclase/cAMP system. Liang and co-workers [Liang, X. P., Lamm, M. E. and Nedrud, J. G. Oral administration of cholera toxin-Sendai virus conjugate potentiates gut and respiratory immunity against Sendai virus. J Immunol. 141, 1495–501, 1988] have shown that glutaraldehyde treatment of CT leads to a 1000-fold reduction in toxicity but preserved capacity to enhance mucosal immune responses after oral immunization. A concomitant loss of ribosyltransferase activity occurred such that with a suitable substrate and necessary co-factors (supplied by lysed red cells) 5–10% residual cyclic AMP was generated compared to untreated toxin.

SUMMARY OF THE INVENTION

The main object of the present invention is to provide DNA-sequences coding for fusion proteins comprising a native or mutant sub-unit of a bacterial toxin that confers enzymatic ADP-ribosylating activity.

Another object of the invention is to provide such DNA-sequences coding for fusion proteins further comprising a stretch of amino acids such that the resulting protein is in possession of water solubility and capability of targeting the fusion protein to a specific cell receptor.

Still another object of the invention is to provide such fusion proteins and compositions containing such fusion proteins for use in improving immune functions.

Yet another object of the invention is to provide recombinant expression vectors harboring the new DNA-sequences and transformed bacterial cells containing such recombinant expression vectors.

For these and other objects that will be clear from the following disclosure the present invention provides for a DNA-sequence comprising a first sequence coding for a native or mutant subunit of a bacterial toxin that confers enzymatic ADP-ribosylating activity, and a second sequence coding for a peptide such that the resulting fusion protein is in possession of water solubility and capability of targeting the fusion protein to a specific cell receptor different from receptors binding to the native toxin, thereby mediating intracellular uptake of at least said subunit.

Said sub-unit is preferably selected from cholera toxin (CT), *E.coli* heat-labile enterotoxin (LT), Pertussis, Clostridia, Shigella and Pseudomonas toxins.

It is particularly preferred that said sub-unit is selected from enterotoxins, such as cholera toxin and heat-labile enterotoxin.

According to a preferred embodiment of the invention said sub-unit is constituted by the sub-unit A1 of cholera toxin or a mutant thereof.

In the fusion protein expressed by a DNA-sequence according to the present invention the peptide thereof is suitably selected from peptides targeting for receptors of cells capable of antigen presentation expressing MHC Class I and Class II.

By way of example, said peptide can be selected from peptides targeting for receptors of lymphocytes and monocytes, or from peptides targeting for receptors of macrophages, dendritic cells, Langerhans cells, and epithelial and endothelial cells. It is particularly preferred that said peptide is selected from peptides targeting for receptors of B lymphocytes.

Examples of specific targeting peptides are peptides capable of binding to receptors of:

(i) granulocyte-macrophage colony-stimulating factor (GM-CSF) capable of binding to the GM-CSF receptor α/β heterodimer present on monocytes, neutrophils, eosinophils, fibroblasts and endothelial cells, (ii) CD4 and CD8 expressed on T cells which together with the T cell receptor (TcR) act as co-receptors for MHC class II and MHC class I molecules,respectively. MHC class I are expressed on most nucleated cells, whereas MHC class II molecules are expressed on dendritic cells, B cells, monocytes, macrophages, myeloid and erythroid precursor cells and some epithelial cells, (iii) CD 28 and CTLA-4, two homodimeric proteins expressed mainly on T cells which bind to B7 expressed on B cells, (iiii) CD40 present mainly on the surface of mature B cells which interact with gp39 expressed on T cells, (iiiii) different isotypes of the Ig heavy chain constant regions which interact with a number of high or low affinity Fc receptors present on mast cells, basophils, eosinophils, platelets, dendritic cells, macrophages, NK cells and B cells.

According to a particularly preferred embodiment of the invention said peptide is constituted by protein A or a fragment thereof in single or multiple copies.

The invention also provides for fusion proteins comprising a sub-unit of a native or mutant bacterial toxin that confers enzymatic ADP-ribosylating activity, and, covalently linked thereto, a peptide such that the resulting fusion protein is in possession of water solubility and capability of targeting the fusion protein to a specific cell receptor different from receptors binding to the native toxin, thereby mediating intracellular uptake of at least said sub-unit.

Furthermore, the invention provides for fusion proteins as defined above in admixture with or covalently linked to an antigen. The invention also covers compositions for use in improving immune functions, such as potentiating immune response, such compositions comprising a fusion protein or an admixture as defined above in an effective amount in combination with a pharmaceutically acceptable diluent or carrier.

Finally, the invention provides for recombinant exression vectors and transformed bacterial cells containing DNA-sequences as defined above.

DETAILED DESCRIPTION OF THE INVENTION

Although the invention is by no means limited hereto it will be exemplified in the following mainly with reference to the sub-unit A1 of cholera toxin or a mutant thereof. Accordingly, the invention will be described in relation to the construction of genetic fusion proteins between CTA1 and molecules which will target the fusion protein to specific cells, such as B cells, macrophages, other antigen-presenting cells or T-cells, and it will be demonstrated herein that such fusion proteins strongly augment immune response in different experimental systems.

One fusion protein denoted CTA1-DD consisting of CTA1 linked to DD, a dimer of the D-region of protein A, binds to soluble immunoglobulins as well as the Ig-receptor on B cells. The results demonstrate that this molecule lacks enterotoxic activity, but still effectively ADP-ribosylates target proteins. When used as a parenteral adjuvant CTA1-DD enhances anti-KLH antibody responses and increases KLH T cell priming.

These results demonstrate the possibility to circumvent the toxic effects of CT simply by removing the CTB pentamer, thus excluding the potential interaction resulting in toxicity between the epithelial cell GMl-receptor and CT. The strategy of targeting of the immunomodulating activity of CTA1 to defined cell populations can be expanded to include essentially any given cell type, enabling specific modulation of cellular responses controlled by cAMP, provided that a suitable targeting molecule is available. CTA1 alone is highly insoluble in physiological aquous solutions. Thus, the targeting molecule used as fusion partner in this invention also has the important function to enhance solubility of the CTA1 entity.

The CTA1 moiety in CTA1-DD is targeted to B cells primarily, and away from the GMl-receptor on e.g. the gut epithelial cells. Furthermore, using this construct we have demonstrated that (i) the enzymatic activity of CTA1 was retained in CTA1-fusion proteins provided that CTA1 was fused at its carboxy terminus;

(ii) CTA1 in the fusion protein exerts its ADP-ribosyltransferase activity in target cells through a pathway for entry that is different from the surface ganglioside GMl-receptor; and that (iii) CTA1-DD displays a strong immunopotentiating activity.

Similarly, CTA1 may be fused to other targeting molecules such as e.g. CD4 to access MHC II expressing cells or any other ligand that specifically can bind to a receptor present on the cell surface. Using this approach CTA1 will not interact with the GMl-receptor present on most mammalian cells including gut epithelial cells because the CTB portion is lacking in the construct. There fore, CTA1 is given a narrow spectrum of cellular interactions via specific binding to surface Ig or Fc-receptors thereby targeting CTA1 to primarily B cells, and macrophages and other Fc-receptor carrying cells.

The compositions for use in improving immune functions, such as potentiating immune response, comprise a fusion protein, either such, or in admixture with or covalently linked to an antigen, in combination with a pharmaceutically acceptable diluent or carrier. The compositions according to the invention will in practice normally be administered topically, orally or by rectal administration or by injection.

For oral administration tablets and capsules may contain conventional excipients, such as binders, for example syrup, sorbitol, or polyvinyl pyrrolidone; fillers, for example lactose, microcrystalline cellulose, corn starch, calcium phosphate or sorbitol; lubricants, for example magnesium stearate, stearic acid, polyethylene glycol or silica; desintegrants, for example potatoe starch or sodium starch glycolate, or surfactants, such as sodium lauryl sulphate.

Oral liquid preparations can be in the form of for example water or oil suspensions, solutions, emulsions, syrups or elixirs, or can be supplied as a dry product for constitution with water or another suitable vehicle before use.

A composition according to the invention can be formulated for parenteral administration by injection or continuous infusion. Compositions for injection can be provided in unit dose form and can take a form such as suspension, solution or emulsion in oil or aqueous carriers and can contain formulating agents, such as suspending, stabilizing and/or disperging agents. Alternatively, the active constituent can be present in powder form for constitution with a suitable carrier, for example sterile pyrogen-free water, before use.

The compositions according to the invention can contain between 0.1 and 99% by weight of the active constituent, suitably from 30 to 95% for tablets and capsules and 3 to 50% for liquid preparations.

BRIEF DESCRIPTION OF THE DRAWINGS

The invention will now be further described by non-limiting specific examples with reference to the appended drawings, wherein.

EXAMPLE 1

Figure 1:
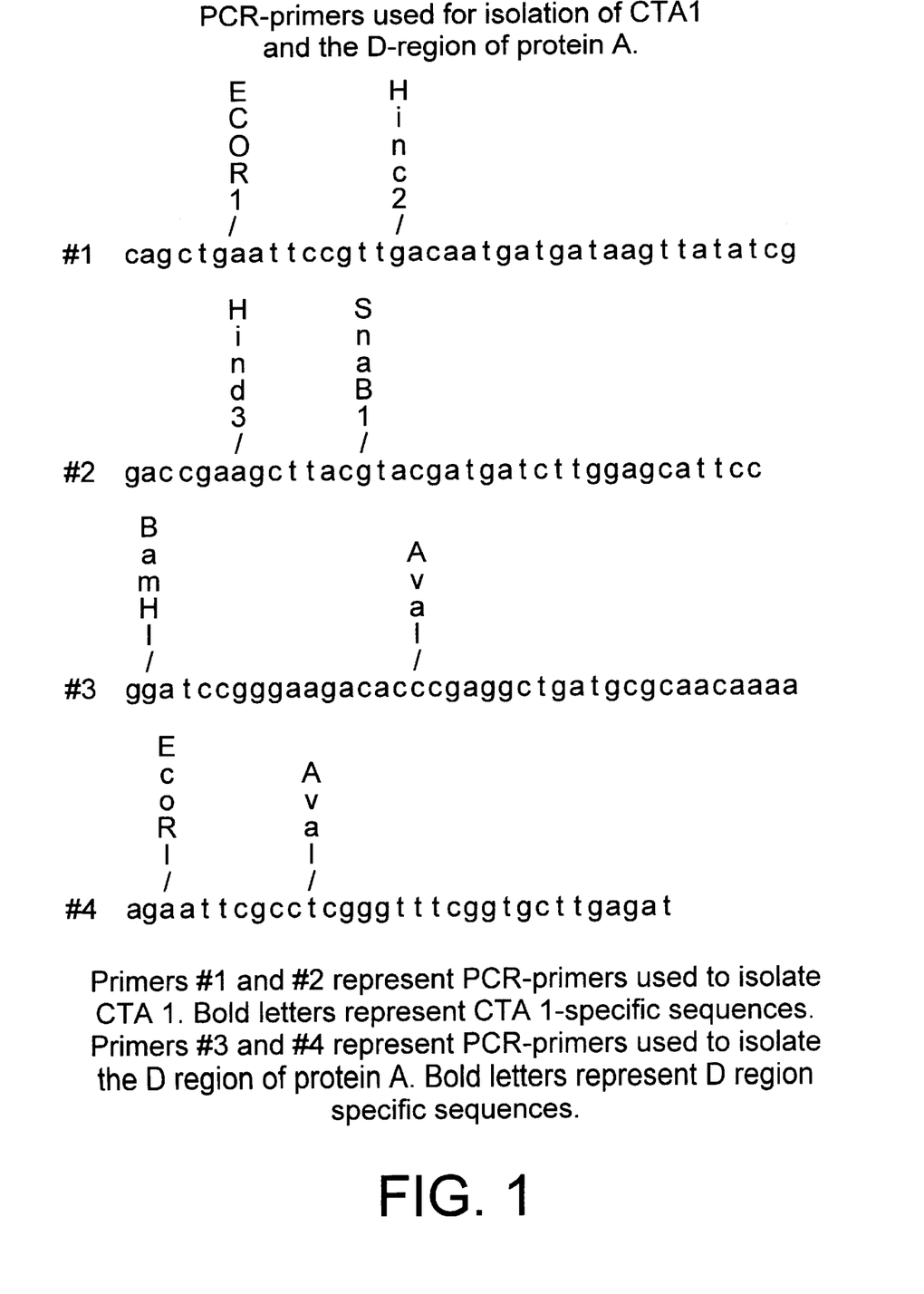
FIG. 1 illustrates PCR-primers used for isolation of CTA1 and the D-region of protein A, primers 1–4 are SEQ ID Nos. 1–4, respectively.
Figure 2:
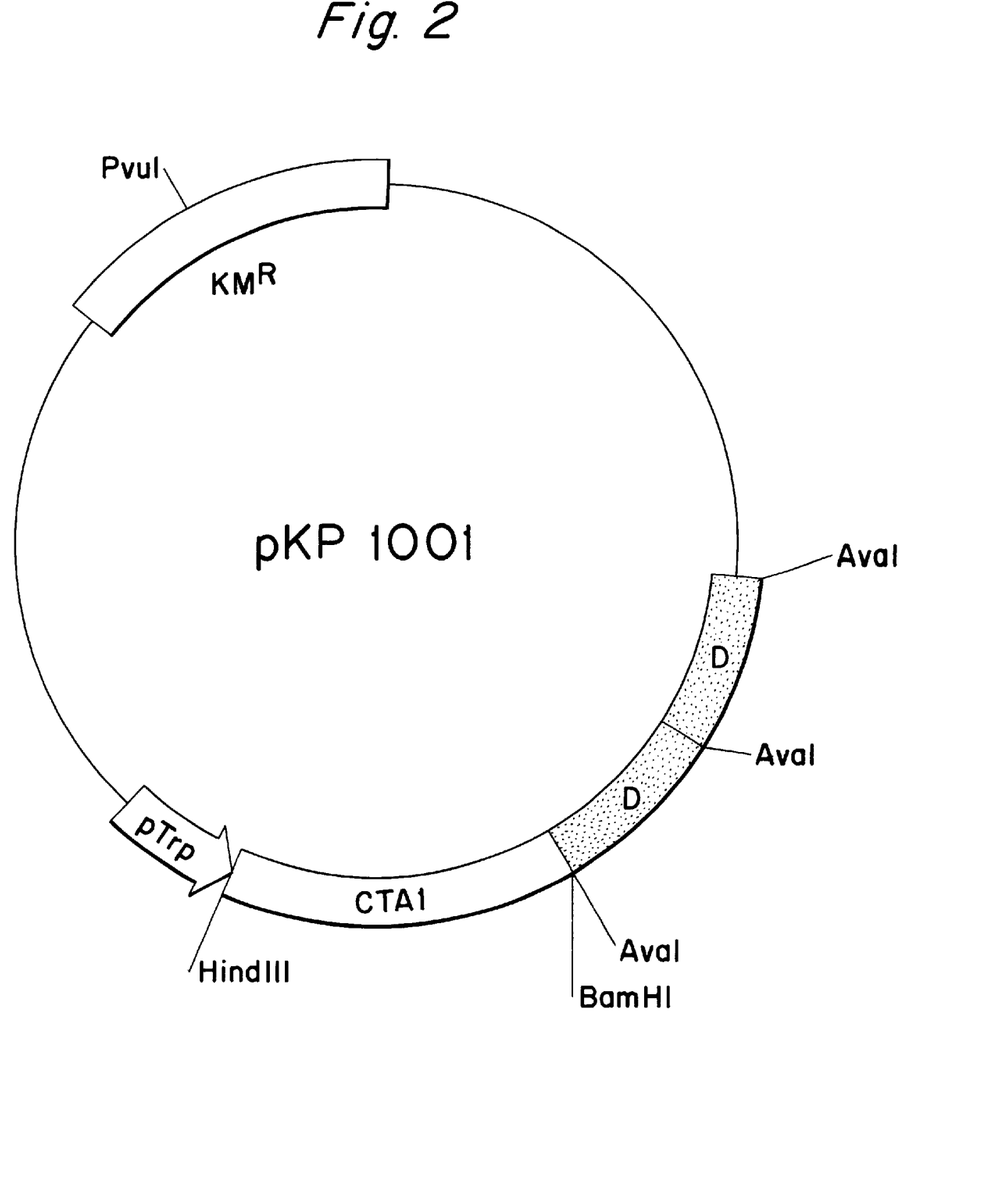
FIG. 2 is a schematic reepresentation of plasmid pKP1001.
Figure 2A:
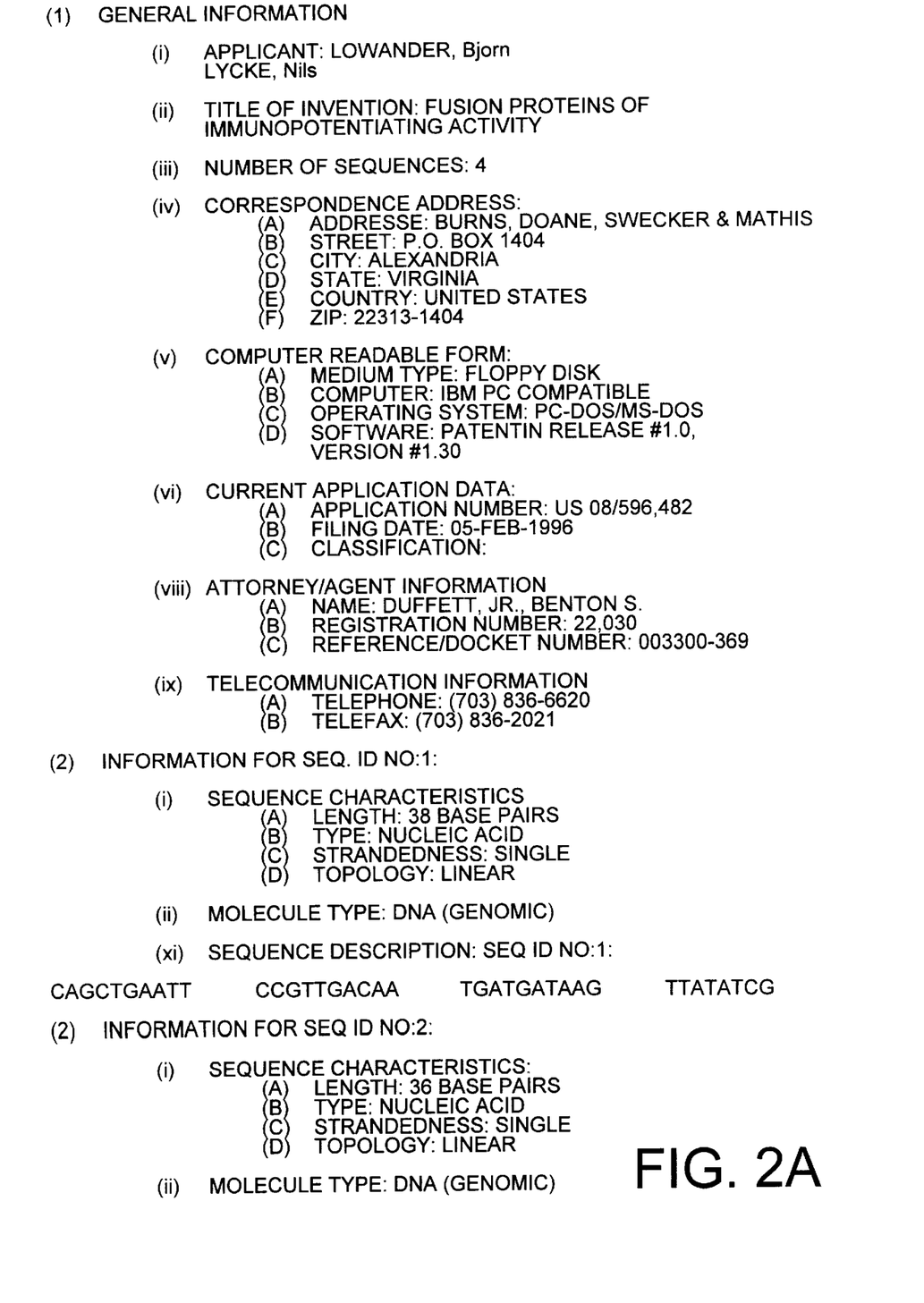
Figure 2B:
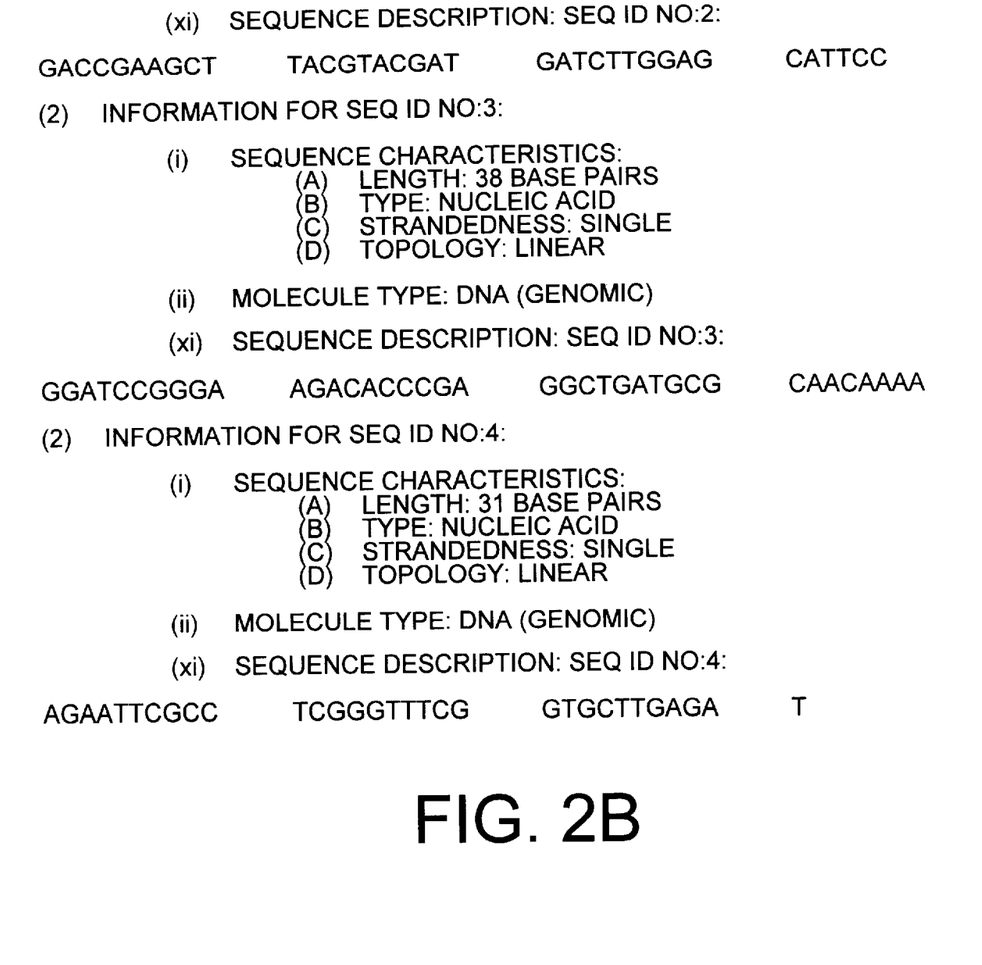

Preparation of a Cholera Toxin A1 Subunit (CTA1) Fusion Protein

*Escherichia coli* strains HB101 and *E.coli* RV308 were used as bacterial hosts for all cloning and expression work. Standard plasmids and vectors used were: pUC 19 and the PCR™ vector (Invitrogen, USA). Restriction enzymes and T4 DNA ligase (Boehringer Mannheim, Germany and New England Biolabs, USA) were used according to the recommendation of the supplier.

The oligonucleotides used in the polymerase chain reaction (PCR) were synthezised with an automated machine (Pharmacia-LKB Gene Assembler Plus, Pharmacia Uppsala, Sweden) and phosphorylated separately using polynucleotide kinase (New England Biolabs, USA). Low melting temperature agarose (NUSIEVE® GTG, FMC Bioproducts, USA) was used to isolate DNA fragments, and Multi Purpose agarose (Boehringer Mannheim, Germany) for DNA analysis.

The PCR amplifications were performed using the DNA Thermal cycler and Taq DNA polymerase (Perkin-Elmer Cetus Instruments, USA).

The bacterial strains were grown in Luria Bertani medium (LB) or yeast tryptone medium (2×YT) with ampicillin (Ap) 50 μg/ml or kanamycin (Km) 100 μg/ml. Plasmid DNA was prepared according to MAGIC® Minipreps DNA Purification Systems manual (Promega, USA).

To determine the nucleotide sequence of the obtained fragments, DNA sequencing was performed using the Sanger method [Sanger, F., Nicklen, S. and Coulson, A. R. DNA sequencing with chain-terminating inhibitors. Proc Natl Acad Sci U S A. 74, 5463–7, 1977.22]. Both strands were sequenced according to a standard protocol for the Taq DYEDEOXY® Terminator cycle sequencing kit (Applied Bio-systems, USA). Analysis were performed on an Applied Biosystems Model 373A DNA Sequencing system.

The gene encoding cholera toxin A1 subunit amino acids 1 to 186 [Mekalanos, J. J., Swartz, D. J., Pearson, G. D., Harford, N., Groyne, F. and de, W. M. Cholera toxin genes: nucleotide sequence, deletion analysis and vaccine development. Nature. 306, 551–7, 1983.] was obtained by PCR using two synthetic DNA primers (#1 and #2, FIG. 1). Similarly the DNA segment encoding the IgG-binding region D of staphylococcus aureus protein A [Uhlén, M., Guss, B., Nilsson, B., Gatenbeck, S., Philipson, L. and Lindberg, M. Complete Sequence of the Staphylococcal Gene Encoding Protein A. J. Biol. Chem. 1984] was obtained by PCR using two synthetic DNA primers (#3 and #4, FIG. 1).

Using standard molecular biology techniques as described in [Sambrook, J. and al., e. Molecular Cloning—A Laboratory Manual.; Second edition ed.; Cold Spring Harbor Laboratory, Cold Spring Harbor, NY.: 1989], plasmid pKP 1001 (FIG. 2) was constructed. Plasmid pKP 1001 containes the gene encoding CTA1 (aa 1-186) fused in frame with a DNA element encoding two tandem copies of the D region from *S. aureus* protein A. In pKP 1001 the transcription unit encoding the CTA1-DD fusion protein is under control of the tryptophane promoter pTrp.

For the production of the CTA1-DD fusion protein, *E.coli* RV308 and HB101 cells transformed with plasmid pKP1001 were grown in shaker flasks overnight in 2×YT or LB (250 ml or 500 ml), with kanamycin, at 37° C. After culture, the cells were collected by centrifugation. In order to solubilize the intracellularly produced fusion proteins, which precipitated as inclusion bodies, the cell pellet was treated with 6M Guanidine-HCl. After addition of destilled water to 1M Guanidine-HCl to allow the protein to refold, the fusion protein was purified by IgG affinity chromatography using IgG Sepharose (Pharmacia, Sweden). After passage of the solubilized fusion protein through the affinity column the gel was washed with TST (50 mM Tris-HCl, pH 7.4, 150 mM NaCl, 0.05% Tween 20), followed buffered with 10 mM ammonium acetate, pH 4.8. Finally the fusion protein was eluated in 0.2 M acetic acid pH 3.1. The eluted fusion protein was stored in aliquots at −20° C. prior to further use. Two other fusion proteins, one comprising CTA1 fused to DD at its amino terminus (DD-CTA1) and a second (CTA1 (Asp109->Ala)-DD) consisting of a mutant form of CTA1 in which Asp 109 was converted to Ala by PCR-directed in vitro mutagenesis, were prepared in the same way.

EXAMPLE 2

Biochemical Characterization of CTA1 Fusion Proteins

To examine the structural and functional properties of CTA1 or the mutant CTA1(Asp109->Ala) expressed in different fusion proteins we examined their interaction with a panel of CTA1-specific monoclonal antibodies as well as their ADP-ribosyltransferase activity using the cell-independent in vitro agmatin-assay. [Lycke N., Tsuji T. and Holmgren J. The advjuvant effect of Vibrio cholerae and *E.coli* heat labile enterotoxins is linked to the ability to stimulate cAMP. Eur.J. Immunol. 22:2277–2281, 1992; Tsuji T., T Inouc, A. Miyama, K. Okamoto, T. Honda and T. Miwatani. 1990. A single aminoacid substitution in the A subunit of *E.coli* enterotoxin results in a loss of its toxic activity. J.Biol.Chem. 265:22520.]

Serial dilutions of three different Mabs (CT17:13, LTp26:4, ETC:6) specific for different CTA1-epitopes were allowed to react with the CTA1 constructs (100 μg/ml ) adhering to human IgG (5 μg/ml) as the solid phase coating on an ELISA plate. An anti-mouse Ig HRP-conjugated poly-clonal sera was used for detection of bound Mabs. Titers are given as $\log_{10}$-titers and defined as the dilution giving an OD reading of 0.4 above background. Representative values of three experiments are shown in table 1.

TABLE 1

Epitope recognition by CTA1-specific Mabs:

| Construct | CT17:13 | LTp26:4 | ETC:6 | anti-Protein A |
|---|---|---|---|---|
| DD-CTA1 | 0.3 | 0.1 | 0.1 | 1.3 |
| CTA1-DD | 3.6 | 0.9 | 3.1 | 2.6 |
| CTA1-DD (Asp109->Ala) | 0 | 0 | 1.8 | 2.5 |

Next, we analysed the ADP-ribosyltransferase activity using the cell-independent in vitro agmatin-assay [Lycke, 1992 #11; Tsuji, 1990 #5, ibid.].

The results shown in Table 2 demonstrate that by positioning DD in the carboxy-terminal end of CTA1 rather than in the amino-terminal end the construct exhibited ADP-ribosyltransferase activity in this cell-independent in vitro assay. The construct demonstrated a linear dose-response activity in this assay and at most gave 50–75% activity compared to an equimolar dose of whole CT. For comparison we introduced a single amino acid point mutation in CTA1-DD at position Asp109. This molecule was found to have less than 5% activity in the ADF-ribosyl-transferase assay and was subsequently used as a negative control. In summary, CTA1-DD represents a fusion protein in which the structural and functional properties of CTA1 remains largely intact. In contrast, in DD-CTA1 the CTA1 moiety is disrupted as demonstrated by its lack of recognition by any of the CTA1-specific antibodies and its complete enzymatic inactivity. In CTA1(ASp109->Ala)-DD on the other hand, CTA1 seems partially intact and retains a fraction of its ADP-ribosylating activity. This finding clearly demonstrates that not only can the targeting structure be varied to direct CTA1 to different cell populations but the properties of CTA1 may also be modulated with respect to e.g. its specific ADP-ribosylating activity. This may be utilized for instance to control the magnitude of a desired cellular response, or to target the ADP-ribosylating activity to G-proteins other than Gsa that may be involved in, or responsible for, the immunomodulating activity of CTA1.

TABLE 2

ADP-ribosylating activity[a] of CTA1-constructs

| | CT | CTA1-DD | CTA1 (Asp109->Ala) | DDCTA1 |
|---|---|---|---|---|
| 5 mg | 30.844 | 28.958 | 2.584 | 0 |
| 2.5 | 19.534 | 13.862 | 2.073 | 0 |
| 1.25 | 10.790 | 9.574 | 1.656 | 0 |
| 0.63 | 6.188 | 5.444 | 1.350 | 0 |

[a]cpm

EXAMPLE 3

Immunomodulating and Toxic Activity of CTA1 Fusion Proteins

Intravenous injections to mice with key-hole limpet hemocyanin (KLH) admixed with CTA1-DD was given to investigate if this construct provided any enhancement of the serum anti-KLH response. As shown in table 3 the CTA1-DD construct significantly, more than 10-fold, increased the serum anti-KLH response as compared to KLH given alone, demonstrating that indeed CTA1-DD acted as a powerful protein adjuvant. This was also supported by studies addressing whether CTA1-DD enhanced antigen-specific T cell priming as we recently demonstrated for CT-adjuvant [Hörnquist, E. and Lycke, N. Cholera toxin adjuvant greatly promotes antigen priming of T cells. Eur J Immunol. 23, 2136–43, 1993]. In three experiments we observed a significantly increased priming efficiency of KLH-specific T cells if CTA1-DD was added to the parenteral immunization (Table 4). Thus, both T and B cell stimulations by antigen was strongly augmented by the addition of CTA1-DD adjuvant.

TABLE 3

In vivo immunoenhancing effect of CTA1-DD:

| Immunization | anti-KLH log10 titers | anti-CT log10 titers | Tcell responses IFNγU/ml |
|---|---|---|---|
| KLH | 3.1 ± 0.1 | 0 | 3 ± 1 |
| KLH + CT | 5.1 ± 0.2 | 3.5 ± 0.3 | 181 ± 31 |
| KLH + CTA1-DD | 4.4 ± 0.1 | 2.3 ± 0.2 | 28 ± 5 |
| KLH + CTA1-DD (Asp109) | 3.3 ± 0.2 | 0 | 3 ± 2 |

Mice were immunized i.v×2 with 10 days between the injections. KLH (50 mg/dose) was given together with 1 μg/dose of CT, 20 μg/dose of CTA1-DD, 20 μg/dose of CTA1(Asp109->Ala)-DD or PBS. Eight days after the final injection mice were bled and serum was analyzed for specific antibodies by ELISA. Serum dilutions were analyzed and titers were calculated as described in Table 1. T cells were restimulated in vitro with KLH seven days following i.v. injection of a single dose of KLH as described above. The IFNg-production in cultures at day 4 was recorded by IFNg-specific ELISA and used as a measure of T cell priming efficiency. IFNg conc. is expressed as U/ml as calculated from a standard curve generated with recombinant IFNg of known conc. We also tested whether chemical conjugation of the CTA1-DD fusion protein with SPDP to ovalbumine (OVA) would augment the immunogenicity of this protein. Mice were immunized intraperitoneally twice with 100 μg per dose of OVA either conjugated to CTA1-DD or with admixed free CTA1-DD or alone. As shown in table 4 the immunogenicity of OVA was increased by 100-fold with conjugated OVA whereas admixed with CTA1-DD more than a 10-fold increase in immununogenicity was observed. This experiment clearly demonstrates that the adjuvant effect of CTA1-DD is acting to enhance immunogenicity of different unrelated protein antigens.

TABLE 4

CTA1-DD potentiates immunogenicity of protein antigens.

| Immunization with: | Anti-OVA mean titer (arithmetic) |
|---|---|
| OVA | 343 ± 25 |
| OVA + free CTA1-DD | 4803 ± 148 |
| OVA conjugated to CTA1-DD | 35510 ± 2540 |

Finally we have investigated whether CTA1-DD is toxic. To this end we injected CTA1-DD in high doses iv, up to 100 mg/dose, with no clinical effect on the mice. Also, the ligated loop test detecting cAMP-induced fluid accumulation/diarrhea was negative (Table 5). In addition, in contrast to CT the CTA1-DD molecule did not stimulate cAMP in GM1-receptor positive, Ig-receptor negative thymocytes/target cells. Therefore, we conclude that CTA1-DD appears to be a non-toxic and enzymatically active molecule which has significant immunoenhancing effects on both B and T cell responses.

TABLE 5

Toxicity of CTA1-DD fusion proteins:

| Molecule | Intestinal loop test | cAMP induction | Clinical symptoms |
|---|---|---|---|
| PBS | 9 ± 5 | 1.5 ± 0.5 | no |
| CT | 105 ± 12 | 14.5 ± 2.2 | yes |
| CTA1-DD | 11 ± 6 | 1.5 ± 0.5 | no |
| CTA1-DD (Asp109->Ala) | 12 ± 3 | 1.5 ± 1.0 | no |

Toxicity was analysed using the intestinal loop test and the result was expressed as mg/cm of fluid accumulation. Doses of CT were 2.5 mg, CTAI-DD 25.0 mg, CTA1 (Asp109->Ala)-DD 25.0 mg per loop. Fluid accumulation was detected at 4h after challenge. cAMP was analyzed by challenging thymocytes for 1, 3 or 6 hours with the diferent preparations. cAMP increases were determined by a radio-immunoassay (Amersham) and are given as pmol/$10^7$ cells. Values represent 1h, no difference in pattern was seen at 3 or 6h. Clinical sumptoms were monitored regularly after injection of up to 100 mg of CTA1-DD or CTA1(Asp109->Ala)-DD while CT was toxic already at 10–15 mg dose.

The CTA1-DD adjuvant protein has, i) proven that it is possible to introduce ADP-ribsyltransferase activity into the cell via another pathway than the GM1-receptor used by CTB, ii) the adjuvant effect of CT is linked to the CTA1molecule rather than the whole toxin, iii) shown that enterotoxicity and adjuvant function indeed may be separable and that the CTA1-DD molecule represents the first generation of a non-toxic safe adjuvant which will have important implications for vaccine construction in general and oral vaccines in particular.

In addition to the use of CTA1-DD as an immunopotentiating agent in vaccines it is of interest in a large number of pathological conditions including HIV and other diseases by improving immune function. In B cells CTA1-DD may for example improve long term survival and rescue cells from apoptosis giving a more sustained response.

We claim:

1. A DNA sequence encoding for a fusion protein which comprises (i) a first DNA sequence encoding the A1 subunit of a bacterial enterotoxin wherein said enterotoxin is selected from the group consisting of cholera toxin (CT) and E. Coli heat labile enterotoxin (LT); and (ii) a second DNA sequence encoding for a peptide which specifically binds to a receptor expressed on a cell capable of antigen presentation, which cell expresses MHC Class I or Class II antigen wherein said cells are selected from the group consisting of lymphocytes, macrophages, dendritic cells, Langerhans cells and epithelial cells, which fusion protein is water-soluble and specifically binds to a cell receptor recognized by the peptide encoded by the second DNA sequence, and which fusion protein is internalized by a cell which expresses said receptor, wherein said receptor is distinct from the receptor bound by the native enterotoxin which comprises said bacterial A1 enterotoxin subunit, and wherein the only subunit of said enterotoxin comprised in the fusion polypeptide is said A1 subunit.

2. The DNA sequence of claim 1, wherein said bacterial enterotoxin subunit comprises the A1 subunit of cholera toxin.

3. The DNA sequence of claim 1, wherein the antigen-presenting cell is a lymphocyte.

4. The DNA sequence of claim 1, wherein the antigen presenting cell is selected from the group consisting of macrophages, dendritic cells, Langerhans cells, and epithelial cells.

5. The DNA sequence of claim 1, wherein the antigen presenting cell is a B-lymphocyte.

6. The DNA sequence of claim 1, wherein the peptide encoded by the second DNA sequence specifically binds to an Ig or Fc receptor expressed on said antigen presenting cell.

7. The DNA sequence of claim 2, wherein the peptide encoded by the second DNA sequence specifically binds to an Ig or Fc receptor.

8. The DNA sequence of claim 3, wherein the peptide encoded by the second DNA sequence specifically binds to an Ig or Fc receptor expressed by said lymphocytes.

9. The DNA sequence of claim 4, wherein the peptide encoded by the second DNA sequence specifically binds to an Ig or Fc receptor expressed by said antigen presenting cell.

10. The DNA sequence of claim 5, wherein the peptide encoded by the second DNA sequence specifically binds to an Ig or Fc receptor expressed by said B-lymphocyte.

11. The DNA sequence of claim 6, wherein said peptide is selected from the group consisting of protein A, a fragment thereof and multimers thereof.

12. A fusion protein which comprises (i) the A1 subunit of a bacterial enterotoxin wherein said enterotoxin is selected from the group consisting of cholera toxin (CT) and *E. Coli* heat labile enterotoxin (LT); and (ii) a peptide which specifically binds to a receptor expressed on a cell capable of antigen presentation, which cell expresses MHC Class I or Class II antigen wherein said antigen-presenting cell is selected from the group consisting of lymphocytes, macrophages, dendritic cells, Langerhans cells and epithelial cells, and wherein said fusion protein is water-soluble and specifically binds to a cell receptor recognized by said peptide, and which fusion protein is internalized by cells which express said receptor which is different than the receptor bound by the native enterotoxin which contains said A1 enterotoxin subunit, and wherein the only subunit of an enterotoxin comprised in the fusion polypeptide is said A1 subunit.

13. The fusion protein of claim 12, wherein said bacterial A1 enterotoxin subunit comprises the A1 subunit of cholera toxin.

14. The fusion protein of claim 12, wherein the antigen-presenting cell is a lymphocyte.

15. The fusion protein of claim 12, wherein the antigen-presenting cell is selected from the group consisting of macrophages, dendritic cells, Langerhans cells, and epithelial cells.

16. The fusion protein of claim 12, wherein the antigen-presenting cell is a B-lymphocyte.

17. The fusion protein of claim 12, wherein the peptide specifically binds to an Ig or Fc receptor expressed by said antigen-presenting cell.

18. The fusion protein of claim 12, wherein the peptide which specifically binds said antigen-presenting cell is selected from the group consisting of protein A, a fragment thereof, and multimers thereof.

19. A fusion protein which comprises the A1 subunit of cholera toxin fused to one or more copies of protein A or a fragment thereof.

20. The fusion protein of claim 19, wherein the fragment of protein A comprises the D region of said protein A.

21. A transformed bacterial cell which expresses the DNA sequence of claim 1.

22. An expression vector which expresses the DNA sequence of claim 1.

23. A composition which comprises a fusion protein according to claim 12, and a pharmaceutical carrier.

24. The fusion protein of claim 12, wherein said bacterial enterotoxin is cholera toxin (CT) and the peptide which specifically binds said antigen-presenting cell is a dimer of the D region of Staphylococcus protein A.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 38 base pairs
      (B) TYPE: nucleic acid
      (C) STRANDEDNESS: single
      (D) TOPOLOGY: linear    (ii) MOLECULE TYPE: DNA (genomic)

(xi) SEQUENCE DESCRIPTION: SEQ ID NO:1:

CAGCTGAATT CCGTTGACAA TGATGATAAG TTATATCG      38

(2) INFORMATION FOR SEQ ID NO:2:

(i) SEQUENCE CHARACTERISTICS:
      (A) LENGTH: 36 base pairs
      (B) TYPE: nucleic acid
      (C) STRANDEDNESS: single
      (D) TOPOLOGY: linear    (ii) MOLECULE TYPE: DNA (genomic)

(xi) SEQUENCE DESCRIPTION: SEQ ID NO:2:

GACCGAAGCT TACGTACGAT GATCTTGGAG CATTCC      36

(2) INFORMATION FOR SEQ ID NO:3:

(i) SEQUENCE CHARACTERISTICS:
      (A) LENGTH: 38 base pairs
      (B) TYPE: nucleic acid
      (C) STRANDEDNESS: single
      (D) TOPOLOGY: linear    (ii) MOLECULE TYPE: DNA (genomic)

```
   (xi) SEQUENCE DESCRIPTION: SEQ ID NO:3:

GGATCCGGGA AGACACCCGA GGCTGATGCG CAACAAAA                              38

(2) INFORMATION FOR SEQ ID NO:4:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

AGAATTCGCC TCGGGTTTCG GTGCTTGAGA T                                     31
```